(12) United States Patent
Weissler et al.

(10) Patent No.: US 9,322,940 B2
(45) Date of Patent: Apr. 26, 2016

(54) METHOD AND SYSTEM FOR SYNCHRONIZING POSITRON EMISSION TOMOGRAPHY (PET) DETECTOR MODULES

(71) Applicant: KONINKLIJKE PHILIPS N.V., Eindhoven (NL)

(72) Inventors: Bjoern Weissler, Aachen (DE); Pierre Klaus Gebhardt, Aachen (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 107 days.

(21) Appl. No.: 14/378,203

(22) PCT Filed: Feb. 25, 2013

(86) PCT No.: PCT/IB2013/051508
§ 371 (c)(1),
(2) Date: Aug. 12, 2014

(87) PCT Pub. No.: WO2013/128363
PCT Pub. Date: Sep. 6, 2013

(65) Prior Publication Data
US 2015/0014545 A1    Jan. 15, 2015

Related U.S. Application Data

(60) Provisional application No. 61/604,247, filed on Feb. 28, 2012.

(51) Int. Cl.
*G01T 7/00* (2006.01)
*G01G 1/29* (2006.01)
(Continued)

(52) U.S. Cl.
CPC ................. *G01T 7/005* (2013.01); *A61B 6/037* (2013.01); *G01T 1/161* (2013.01); *G01T 1/20* (2013.01); *G01T 1/2985* (2013.01)

(58) Field of Classification Search
CPC ....... G01T 7/005; G01T 1/2985; G01T 1/161; G01T 1/20; A61B 6/037
See application file for complete search history.

(56) References Cited

U.S. PATENT DOCUMENTS 4,249,266 A * 2/1981 Nakamori ............ H04B 10/40
358/901.1
7,180,074 B1 * 2/2007 Crosetto ............... G01T 1/1611
250/370.09
(Continued)

FOREIGN PATENT DOCUMENTS

WO    2005052635 A2    6/2005

OTHER PUBLICATIONS

Aliaga, R. J., et al.; PET System Synchronization and timing Resolution Using High-Speed Data Links; 2011; IEEE Trans. on Nuclear Science; 58(4)1596-1605.
(Continued)

*Primary Examiner* — David Porta
*Assistant Examiner* — Mindy Vu

(57) ABSTRACT

A detector module (50) for a positron emission tomography (PET) system (10) includes an optical transceiver (66) receiving an optical data stream from a PET processing system (48). The data stream includes a pulse train carrying a command to generate sync/reset pulses. The system (10) further includes synchronization circuitry (70) configured to simultaneously jitter clean the pulse train and one of: 1) count the pulses of the pulse train; and 2) monitor the pulse train for a missing pulse. The synchronization circuitry (70) is further configured to, in response to counting a predetermined number of pulses or detecting the missing pulse, extract a jitter clean pulse from the pulse train to generate a jitter clean sync/reset pulse. The system (10) further includes an internal clock (64) which receives the jitter clean sync/reset pulse.

19 Claims, 5 Drawing Sheets

(51) Int. Cl.
    *G01T 1/161*     (2006.01)
    *G01T 1/20*     (2006.01)
    *G01T 1/29*     (2006.01)
    *A61B 6/03*     (2006.01)

(56) References Cited

U.S. PATENT DOCUMENTS

| | | |
|---|---|---|
| 7,627,086 B2 | 12/2009 | Vogtmeier |
| 2007/0101242 A1 * | 5/2007 | Yancey ............... G06F 13/4256 714/776 |

OTHER PUBLICATIONS

Grant, A. M., et al.; All-optical encoding of PET detector signals; 2011; IEEE Nuclear Science Symposium Conference Record; pp. 2258-2260.

Junnarkar, S. S., et al.; FPGA based self calibrating 40 picosecond resolution, wide range Time to Digital Converter; 2008; IEEE Nuclear Science Symposium Conference Record; pp. 3434-3439.

* cited by examiner

METHOD AND SYSTEM FOR SYNCHRONIZING POSITRON EMISSION TOMOGRAPHY (PET) DETECTOR MODULES

CROSS REFERENCE TO RELATED APPLICATIONS

This application is a national filing of PCT application Serial No. PCT/IB2013/051508, filed Feb. 25, 2013, published as WO 2013/128363 A2 on Sep. 6, 2013, which claims the benefit of U.S. provisional application Ser. No. 61/604,247 filed Feb. 28, 2012, which is incorporated herein by reference.

The present application relates generally to nuclear medical imaging. It finds particular application in conjunction with positron emission tomography (PET) and will be described with particular reference thereto. However, it is to be understood that it also finds application in other usage scenarios and is not necessarily limited to the aforementioned application.

In PET, pairs of gamma photons are concurrently detected to define a line of response (LOR). The time at which each photon is detected is used to identify concurrent pairs. In time of flight (TOF) PET, the relative detection times of each concurrent pair are used to localize the radiation event along the LOR. Because the gamma photons travel at the speed of light, detection times are measured with nanosecond resolution.

Increasingly, PET systems are employing solid state PET detector modules for detection, where the detector modules are positioned encircling a region of interest. Each detector module detects gamma photon strikes, digitizes the events and sends the digitized events with corresponding time stamps to a PET backend. The time stamps are then employed to pair photon strikes and localize the radiation event along the LOR.

For accurate time measurement, the PET detectors are synchronized, typically within ten picoseconds. All clocks of the PET detectors are synchronized to run at the same speed. This is typically performed by distributing a permanent low jitter reference clock to the PET detectors. Further, a sync/reset pulse is transmitted to the PET detectors to check the synchronization or to reset the clocks. Known PET systems employing solid state PET detectors use galvanic cables to synchronize reference clocks. These cables increase the size and the cost of PET systems employing solid state PET detectors. Further, in PET/magnetic resonance (MR) systems, it's undesirable to have further galvanic cables.

One solution to overcome these problems is to use optical communication with glass or plastic fibers. However, such as solution requires optical transceivers, which come at the cost of high price and high power consumption. Further, a large amount of space is needed. Even more, optical transceivers have poor jitter for TOF PET. Hence, it is preferable to reduce the amount of optical transceivers. The present application provides new and improved methods and systems which overcome the above-referenced challenges and others.

In accordance with one aspect, a detector module for a positron emission tomography (PET) system includes an optical transceiver receiving an optical data stream from a PET processing system. The data stream includes a pulse train carrying a command to generate sync/reset pulses. The system further includes synchronization circuitry configured to simultaneously jitter clean the pulse train and one of: 1) count the pulses of the pulse train; and 2) monitor the pulse train for a missing pulse. The synchronization circuitry is further configured to, in response to counting a predetermined number of pulses or detecting the missing pulse, extract a jitter clean pulse from the pulse train to generate a jitter clean sync/reset pulse. The system further includes an internal clock which receives the jitter clean sync/reset pulse.

In accordance with another aspect, a method for synchronizing a detector module with other detector modules of a positron emission tomography (PET) system is provided. The method includes optically receiving an optical data stream from a PET processing system. The data stream includes a pulse train carrying a command to generate sync/reset pulses. The method further includes simultaneously jitter cleaning the pulse train and one of: 1) counting the pulses of the pulse train; and 2) monitoring the pulse train for a missing pulse. In response to counting a predetermined number of pulses or detecting the missing pulse, a jitter clean pulse is extracted from the pulse train to generate a jitter clean sync/reset pulse. The jitter clean sync/reset pulse is provided to an internal clock.

In accordance with another aspect, a positron emission tomography (PET) system includes a PET processing system which generates a clock signal and sync/reset pulse information and which reconstructs a PET image from received event data. The PET processing system includes optical transceivers which convert the clock signal and the sync/reset pulse information into an optical data stream and which convert optical event information into the received event data. The PET system further includes a plurality of detector modules disposed to received gamma photons form an examination region. Each detector module includes a transceiver which converts light signals to electrical signals, synchronization circuitry which extracts the clock signal and the sync/reset pulses from the electrical signals, a clock which is sync/reset with the clock signal and the sync/reset pulses, and a detector grid which converts the received gamma photons into event data. The transceiver further converts the event data and information of locations at which the gamma photon were received and a time stamp from the clock into the optical event information. The PET system further includes a plurality of optical fibers connecting the PET processing system with each of the detector modules to carry the optical data stream simultaneously to the detector modules and the optical event information from each detector module to the PET processing system.

One advantage resides in reduced size and cost.

Another advantage resides in a reduced number of galvanic connections.

Another advantage resides in low jitter clock signals and sync/reset pulses.

Still further advantages of the present invention will be appreciated to those of ordinary skill in the art upon reading and understand the following detailed description.

The invention may take form in various components and arrangements of components, and in various steps and arrangements of steps. The drawings are only for purposes of illustrating the preferred embodiments and are not to be construed as limiting the invention.

Figure 1:
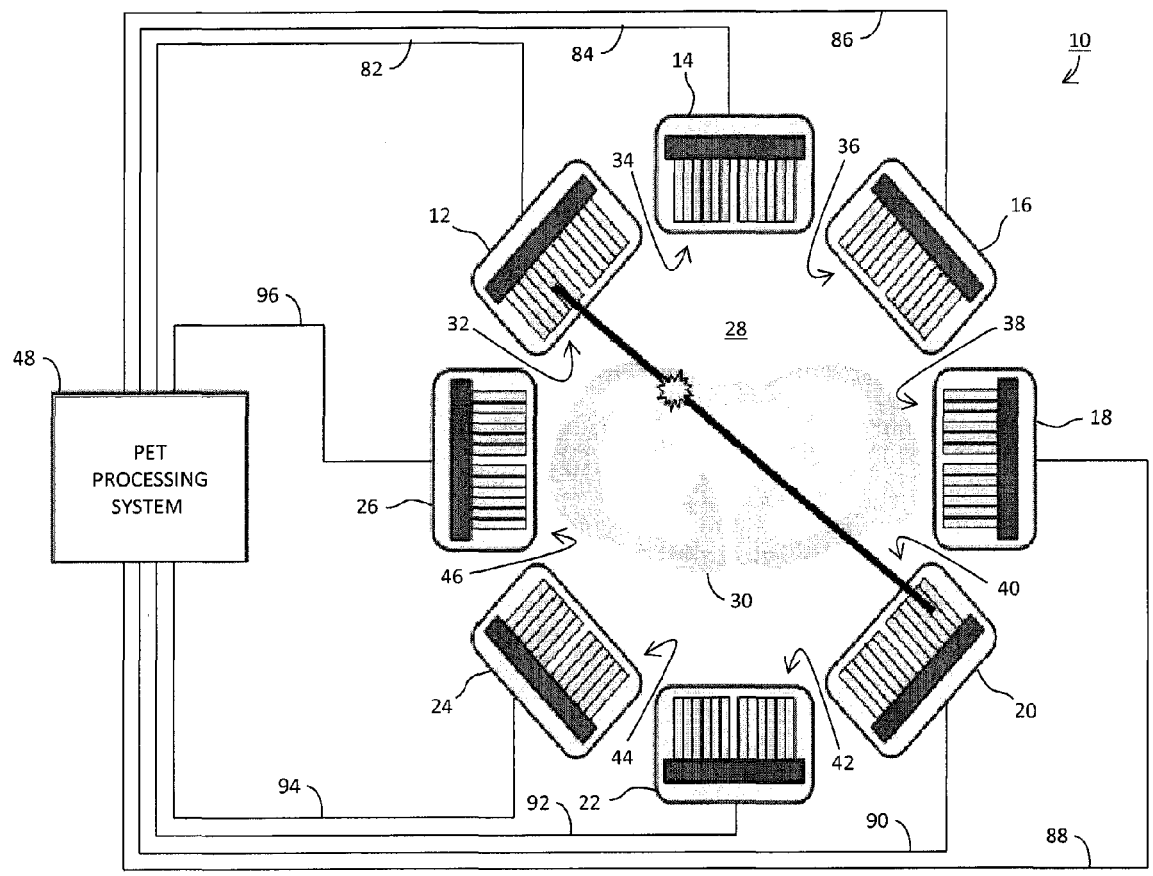
FIG. 1 illustrates a positron emission tomography (PET) system employing solid state detector modules.

With reference to FIG. 1, a positron emission tomography (PET) system 10 includes a plurality of solid state detector modules 12, 14, 16, 18, 20, 22, 24, 26 arranged, typically in a circle, around an imaging volume 28 for receiving a region of interest (ROI) 30 of a patient to image. Further, the PET system 10 can include a patient support (not shown), such as a patient bed, to support the patient and/or position the ROI 30 in the imaging volume 28. Examples of the ROI 30 include, but are not limited to, hearts, brains, thyroids, bones, joints, ligaments, tendons, muscles, nerves, kidneys, lungs, tumors, lesions, and so on.

Before imaging, the ROI 30 is injected with one or more radioisotopes. Examples of such radioisotopes include, but are not limited to, Tc-99m, 1-131, Ga-67, and In-111. The radioisotopes can be combined and injected with radioligands to create a radiopharmaceutical that binds to or is preferentially absorbed by specific types of tissue. The ROI 30 is then positioned in the imaging volume 28. For example, the patient is positioned on the patient support and the patient support moves the ROI 30 into the imaging volume 28.

The detector modules 12, 14, 16, 18, 20, 22, 24, 26 receive gamma photons emitted by the radioisotopes injected into the ROI 30 during imaging. The received gamma photons strike receiving faces 32, 34, 36, 38, 40, 42, 44, 46 of the detector modules 12, 14, 16, 18, 20, 22, 24, 26. For example, as illustrated a pair of gamma photons are emitted from the ROI 30 and strike a first detector module 12 and a second detector module 20 near simultaneously. The detector modules 12, 14, 16, 18, 20, 22, 24, 26 then digitize these events and send the digitized events with corresponding time stamps to a PET processing system 48 of the PET system 10. The digitized events suitably identify the location of the corresponding gamma photon strikes on the receiving faces 32, 34, 36, 38, 40, 42, 44, 46, the receiving detector, energy of the event and the time stamp. As discussed hereafter, using the time stamps, the PET processing system 48 pairs events and performs image reconstruction.

Figure 2:
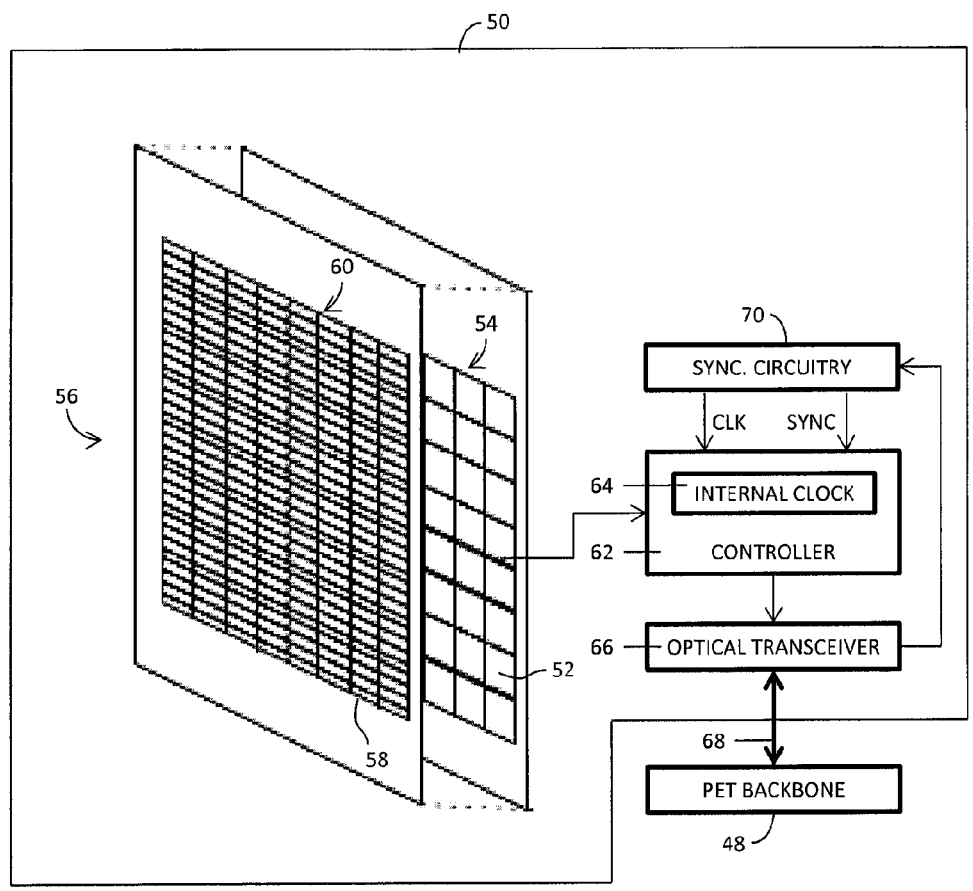
FIG. 2 illustrates a detector module.

With reference to FIG. 2, each 50 of the detector modules 12, 14, 16, 18, 20, 22, 24, 26 includes a plurality of radiation sensitive elements 52. The plurality of radiation sensitive elements 52 define a detection grid 54 for photons, such as gamma photons or visible-light photons. The plurality of radiation sensitive elements 52 can directly or indirectly detect gamma photons. When the plurality of radiation sensitive elements 52 directly detect gamma photons, the detection grid 54 typically defines the receiving face 56 of the detector module 50. For indirect detection, the detector module 50 further includes one or more scintillator elements 58 optically coupled to the detection grid 54 of optical detectors. Hence, the one or more scintillator elements 58 defines the receiving face of the detector module 50. In some instances, the one or more scintillator elements 58 further define a pixelated scintillation grid 60. The pixels of the pixelated scintillation grid 60 are optically correlated with pixels of the detection grid 54 and are typically smaller than the pixels of the detection grid 54. When struck by gamma photons, the one or more scintillator elements 58 emit visible-light photons toward the detection grid 54. The detection grid 54 then detects the visible-light photons as discussed above. Examples of scintillation elements include scintillator plates, individual scintillation crystals (e.g., sodium iodide crystals), and the like. Examples of radiation sensitive elements include digital or analog silicon photomultipliers (SiPMs), photodiodes, opto-electric transducers, direct photon to electrical converters (a.k.a., semiconductor gamma detectors), such as semiconductor crystals, zinc-cadmium telluride (CZT) elements, and the like, and so on.

To digitize detected events, the detector module 50 further includes a controller 62. The controller 62 is electrically connected with the detection grid 54 so as to separately receive electrical pulses from the radiation sensitive elements. In response to receiving an electrical pulse, the controller 62 digitizes the event. This suitably entails determining the location of the event on the detection grid 54 using the known location of the source of the electrical pulse corresponding to the event. The location of the event is then time stamped using an internal clock 64 of the controller 62 and optically transmitted to the PET processing system 48 using an optical transceiver 66 of the detector module 50, the optical transceiver 66 connected to the PET processing system 48 with an optical fiber 68.

As discussed above, the internal clocks of the detector modules 12, 14, 16, 18, 20, 22, 24, 26 need to be synchronized with each other to maintain timing accuracy. A common clock signal and common sync/reset pulses are optically sent simultaneously from the PET processing system 48 to all of the detector modules 12, 14, 16, 18, 20, 22, 24, 26. The common clock signal controls the speed of the internal clocks, and the common sync/reset pulses resets the internal clocks of all the detector modules 12, 14, 16, 18, 20, 22, 24, 26 to a common time. As discussed hereafter, the common clock signal and the common sync/reset pulses can be received directly or indirectly.

Figure 3:
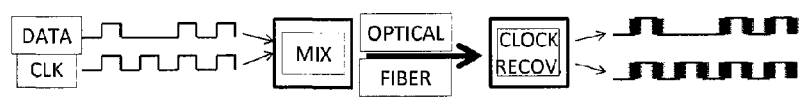
FIG. 3 illustrates clock recovery.

Suitably, the common clock signal and the common sync/reset pulses are received by way of a data stream received from the PET processing system 48. In one instance, the common clock signal is integrated into, or mixed with, the data stream and recovered from the data stream using clock recovery, as illustrated in FIG. 3. Integration can entail, for example, encoding the data stream using 8B/10B, and/or recovery can entail, for example, generating a clock signal from the approximate frequency of the data stream and then phase aligning the clock signal to the transitions in the data stream with a phase-locked loop (PLL). Further, the data stream is employed to transmit the common sync/reset pulses or commands to generate the common sync/reset pulses.

Figure 4:
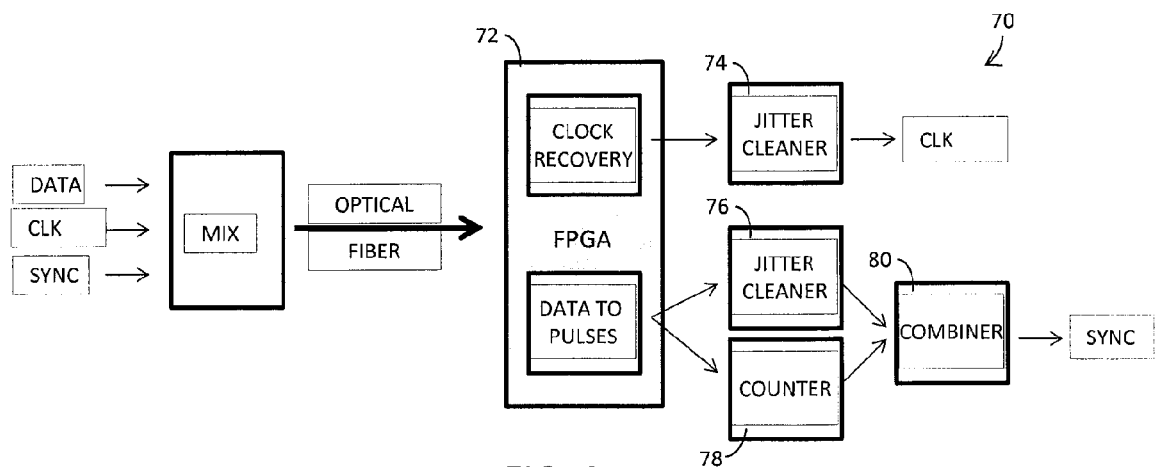
FIG. 4 illustrates synchronization circuitry of a detector module.

Synchronization circuitry 70 of the detector module 50 suitably performs clock recovery and/or generation of the common sync/reset pulses from the data stream. Specifically, as shown in FIG. 4, recovery circuitry 72, such as an field-programmable gate array (FPGA), of the synchronization circuitry 70 does so. Alternatively, it is also contemplated that the controller 62 can do so.

Figure 5:
FIG. 5 illustrates the input and the output of a jitter cleaner.

One challenge with using the optical fiber 68 to transmit the common clock signal and the common sync/reset pulses is that the optical fiber 68 introduces a lot of jitter, which leads to poor synchronization. To address this, attention is further directed to FIG. 4. As shown therein, the recovered common clock signal is passed through a jitter cleaner 74 of the synchronization circuitry 70 that removes the jitter using a local-low-jitter oscillator that locks its frequency and phase onto the recovered common clock signal. FIG. 5 illustrates the input and output of a jitter cleaner. A jitter cleaner only works on a periodical clock signal, not on data or a single sync/reset pulse, and is not well suited for synchronization. The jitter cleaner locks its local oscillator to a reference oscillator.

With continuing attention is directed to FIG. 4, each time the PET processing system 48 resets or synchronizes the internal clocks of the detector modules 12, 14, 16, 18, 20, 22, 24, 26, a periodical sync/reset pulse train of a known length, such as five thousand pulses, is received. As noted above, the sync/reset pulses can be received directly over the data stream or indirectly via command for the recovery circuitry 72 to generate the sync/reset pulse train. The pulse train is then fed into both a jitter cleaner 76 of the synchronization circuitry 70 and into a counter 78 of the synchronization circuitry 70 that counts the pulses. Once a predetermined number, or all of the pulses, are counted, a cleaned sync/reset pulse is generated by a combiner 80 of the synchronization circuitry 70 from the jitter cleaned pulse train at the moment where the jitter cleaned pulse train gives the next pulse.

Figure 6:
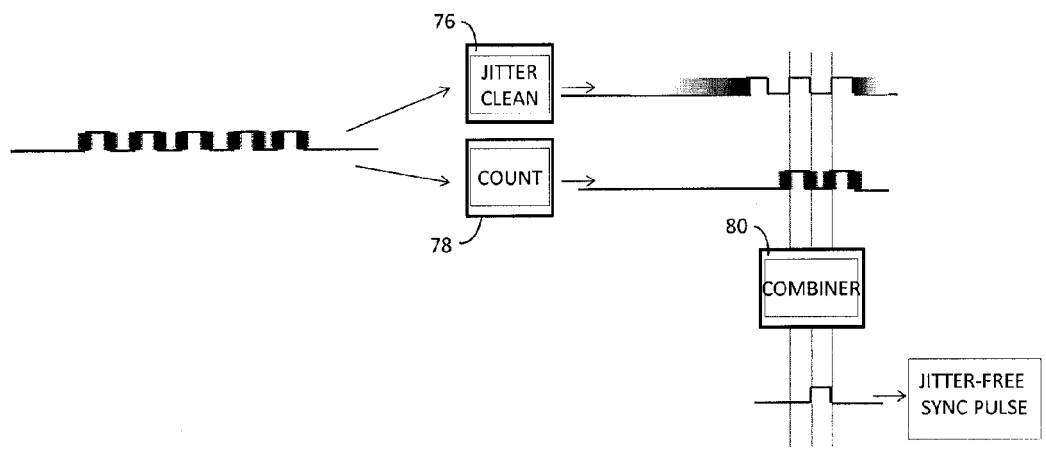
FIG. 6 illustrates the generation of a jitter-free sync pulse.

To illustrate, attention is directed to FIG. 6. A data stream including a periodical pulse train is received of which five pulses are illustrated. The periodical pulse train is then provided to the jitter cleaner 76 and the counter 78. The jitter cleaned pulse train is provided to the combiner 80, but, as noted above, it is unclear when the jitter cleaner 76 locks. The counter 78 counts the pulse train and when it counts to the prescribed number provides two pulses to the combiner 80. Once the combiner 80 gets the count pulses, it generates the sync or reset pulse by inverting the corresponding two pulses of the jitter cleaned pulse train.

In an alternative embodiment, the common sync/reset pulses are determined from a continuous, periodic signal. Namely, the PET processing system 48 sends the continuous, periodic signal over the data stream and, each time the PET processing system 48 resets or synchronizes the internal clocks of the detector modules 12, 14, 16, 18, 20, 22, 24, 26, a pulse is excluded from the continuous, periodic signal. The jitter cleaner 76 cleans the continuous, periodic signal, and a detection circuit monitors for the missing pulse. Upon detecting the missing pulse, the next pulse of the cleaned continuous, periodic signal is output as the cleaned sync/reset pulse.

Figure 7:
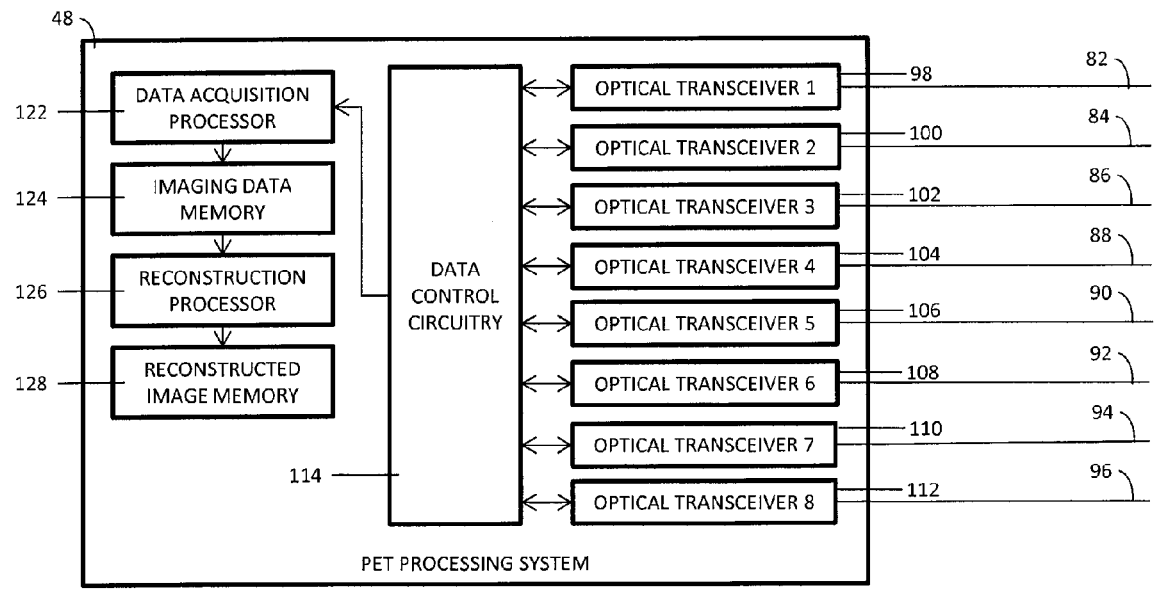
FIG. 7 illustrates a PET processing system.

Referring back to FIG. 1, the PET processing system 48 is optically connected with optical fibers 82, 84, 86, 88, 90, 92, 94, 96 to the detector modules 12, 14, 16, 18, 20, 22, 24, 26 to receive event data from the detector modules 12, 14, 16, 18, 20, 22, 24, 26. With reference to FIG. 7, the PET processing system 48 includes a plurality of optical transceivers 98, 100, 102, 104, 106, 108, 110, 112, one for each of the detector module 12, 14, 16, 18, 20, 22, 24, 26, providing an interface for components of the PET processing system 48 to optically communicate with the detector modules 12, 14, 16, 18, 20, 22, 24, 26. Using the optical transceivers 98, 100, 102, 104, 106, 108, 110, 112, data control circuitry 114 of the PET backbone provides the detector modules 12, 14, 16, 18, 20, 22, 24, 26 with a common clock signal and common sync/reset pulses for synchronization.

As discussed above, the common clock signal controls the speed of the internal clocks of the detector modules 12, 14, 16, 18, 20, 22, 24, 26, and the common clock signal and common sync/reset pulses reset or periodically synchronize the internal clocks to a common value, such as zero. The sync/reset pulses are suitably sent immediately before and/or periodically during imaging the ROI 30 to ensure that the internal clocks of the detector modules 12, 14, 16, 18, 20, 22, 24, 26 are and remain synchronized.

To send the common clock signal and common sync/reset pulses, a data stream is sent to each of the detector modules 12, 14, 16, 18, 20, 22, 24, 26. The data stream is integrated, or mixed, with the common clock signal and clock recovery is used to recover the common clock signal from the data stream. To better facilitate clock recovery, the data stream can be encoded to increase transitions using, for example, 8B/10B encoding. Further, the data stream includes the common sync/reset pulses or commands to generate the common sync/reset pulses. Alternatively, the data stream includes a continuous, periodical signal missing a pulse, the missing pulse indicating sync/reset.

Figure 8:
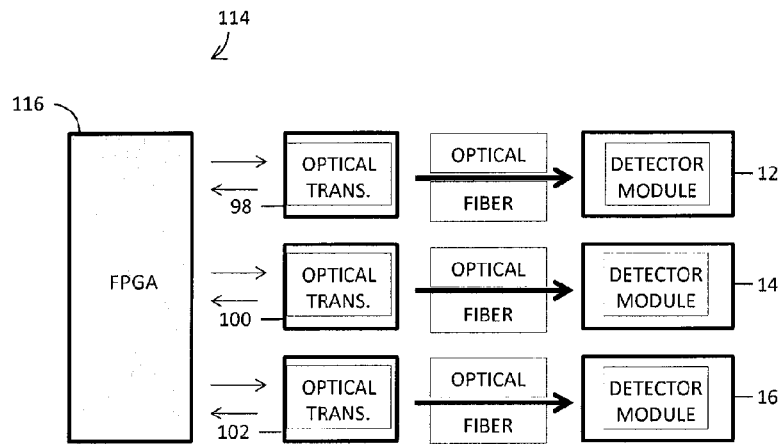
FIG. 8 illustrates a first approach for distributing a clock signal and sync/reset pulses to a plurality of detector modules.
Figure 9:
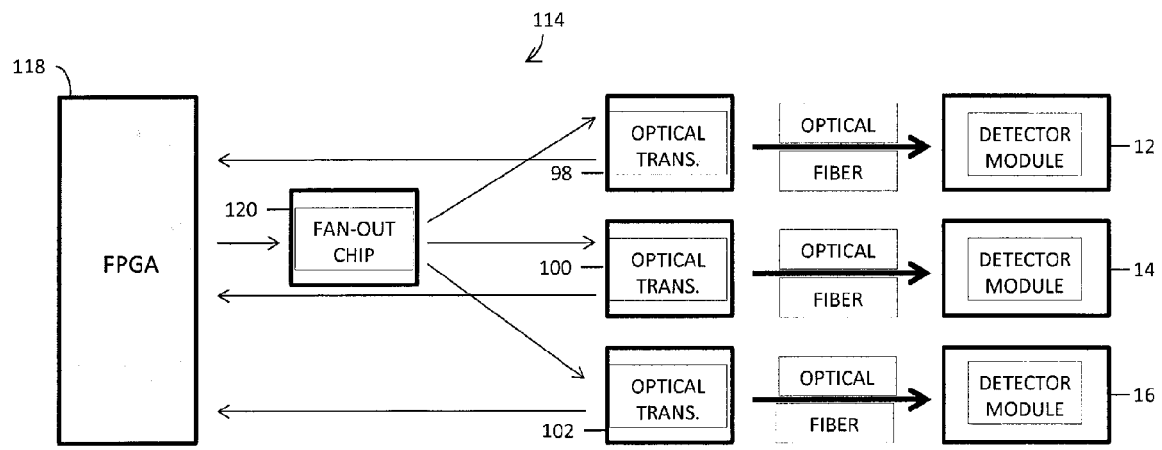
FIG. 9 illustrates a second approach for distributing a clock signal and sync/reset pulse to a plurality of detector modules.

In one embodiment, the data control circuitry 114 includes control circuitry 116, such as an FPGA, generating and providing the common clock signal and the common sync/reset pulses to each of the detector modules 12, 14, 16, 18, 20, 22, 24, 26 via the corresponding optical transceiver 98, 100, 102, 104, 106, 108, 110, 112, as illustrated in FIG. 8. In another embodiment, the data control circuitry 114 includes control circuitry 118, such as an FPGA, generating the common clock signal and the common sync/reset pulses and distribution circuitry 120, such as a fan-out chip, providing the common clock signal and the common sync/reset pulses to each of the detector modules 12, 14, 16, 18, 20, 22, 24, 26 via the corresponding optical transceiver 98, 100, 102, 104, 106, 108, 110, 112, as illustrated in FIG. 9.

During imaging, a data acquisition processor 122 of the PET backbone uses the optical transceivers 98, 100, 102, 104, 106, 108, 110, 112 to collect event data for a plurality of events from the detector modules 12, 14, 16, 18, 20, 22, 24, 26. Typically, the event data is acquired through the data control circuitry 114. Data acquisition is performed over a selected period of time, such as ten minutes. For each detection event, the detection event data typically includes a location of the detection event on the corresponding detection grid and information of the detector, an energy of each event, and a time stamp. The event data is stored in an imaging memory or buffer 124 of the system 10. A reconstruction processor 126 of the PET backbone processes the data from the imaging data memory 124 into a three-dimensional image representation. This includes filtering invalid events, pairing events based on the time stamps to define line of responses (LORs), and reconstructing the LORs into an image representation. In time of flight (TOF) PET, the time stamps associated with each LOR are used to localize the annihilation event which cased the gamma photon pair along the LOR. The image representation is stored in a reconstruction image memory 126 of the system 10 for subsequent use. For example, the three-dimensional image can be employed by a video processor and/or displayed on a display.

Figure 10:
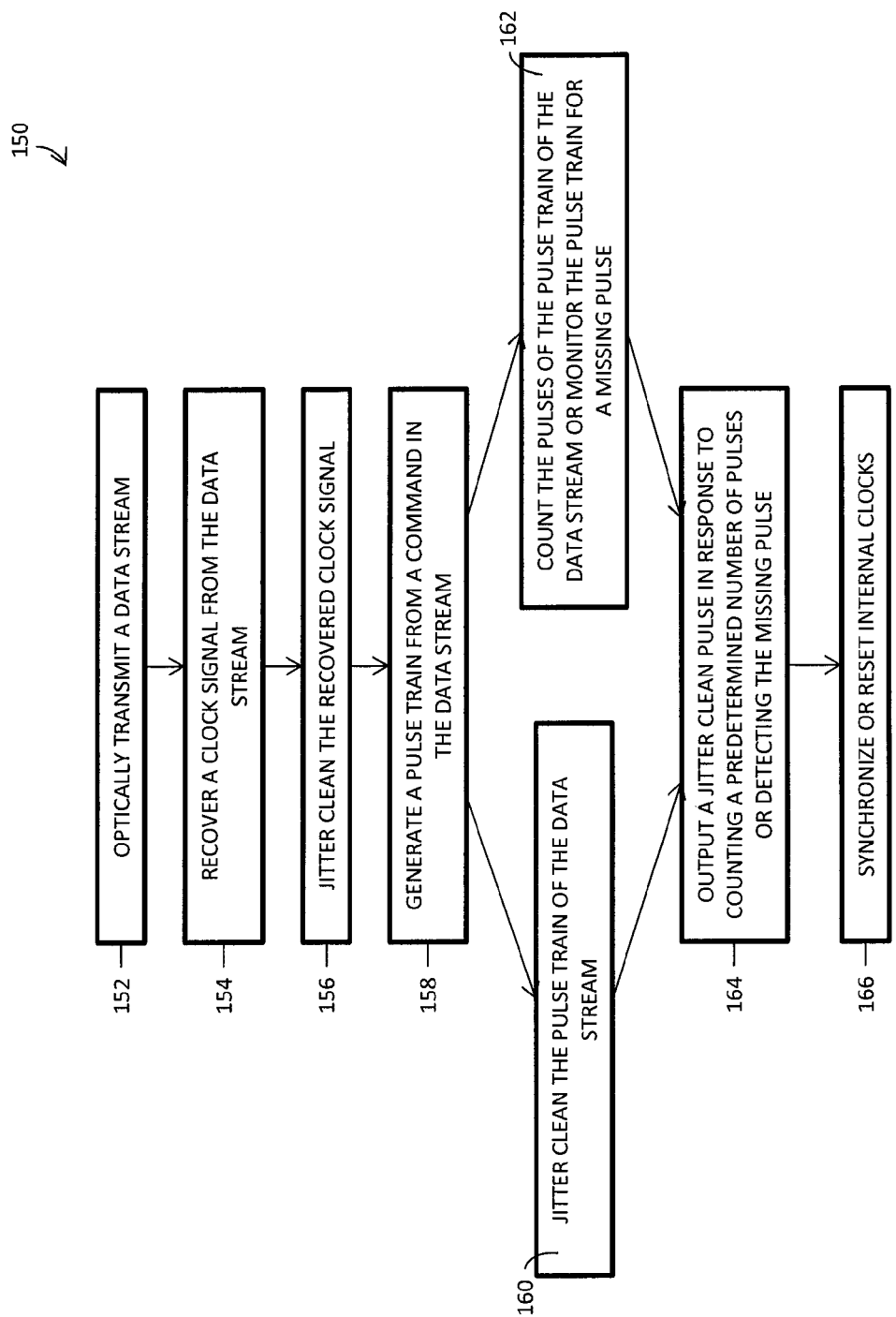
FIG. 10 illustrates a method for synchronizing a detector module with other detector modules of a PET system.

With reference to FIG. 10, a method 150 for synchronizing each 50 one of the detector modules 12, 14, 16, 18, 20, 22, 24, 26 with other ones of the detector modules 12, 14, 16, 18, 20, 22, 24, 26 is provided. The method 150 is suitably performed by each 50 of the detector modules 12, 14, 16, 18, 20, 22, 24, 26 near simultaneously using the same clock signal and pulse train of sync/reset pulses. The method 150 includes optically transmitting 152 a data stream from the PET processing system 48 over optical paths, preferably of equal length so that the optical data stream takes the same time to travel from the PET processing system 48 to every detector module. The data stream includes the pulse train of a predetermined length, such as five thousand pulses.

At each detector module, the clock signal is recovered 154 from the data stream using clock recovery and jitter cleaned 156 to generate a jitter-free clock signal. A pulse train which carries the sync/reset information is extracted 158 from the data stream. Then, the pulse train is jitter cleaned 160 while, in one embodiment, simultaneously counting 162 the pulses of the pulse train. In response to counting a predetermined number of pulses, the next pair of pulses of the cleaned pulse train are inverted and output 164 as a cleaned sync/reset pulse. In another embodiment, the jitter-free clock pulse stream is monitored 162 for a missing pulse and the next pulse after the missing pulse is output as the sync pulse 160. The internal clocks of all of the detector modules 12, 14, 16, 18, 20, 22, 24, 26 are synchronized or reset 166 in response to the cleaned sync/reset pulse.

As used herein, a memory includes one or more of a non-transient computer readable medium; a magnetic disk or other magnetic storage medium; an optical disk or other optical storage medium; a random access memory (RAM), read-only memory (ROM), or other electronic memory device or chip or set of operatively interconnected chips; an Internet/Intranet server from which the stored instructions may be retrieved via the Internet/Intranet or a local area network; or so forth. Further, as used herein, a processor includes one or more of a microprocessor, a microcontroller, a graphic processing unit (GPU), an application-specific integrated circuit (ASIC), an FPGA, and the like; a user input device includes one or more of a mouse, a keyboard, a touch screen display, one or more buttons, one or more switches, one or more toggles, and the like; a database includes one or more memories; controller includes a processor and, optionally, a memory; and a display device includes one or more of a LCD display, an LED display, a plasma display, a projection display, a touch screen display, and the like.

The invention has been described with reference to the preferred embodiments. Modifications and alterations may occur to others upon reading and understanding the preceding detailed description. It is intended that the invention be construed as including all such modifications and alterations insofar as they come within the scope of the appended claims or the equivalents thereof.

The invention claimed is:

1. A detector module for a positron emission tomography (PET) system, said detector module comprising:
    an optical transceiver receiving an optical data stream from a PET processing system, the data stream including a pulse train carrying a command to generate sync/reset pulses;
    synchronization circuitry configured to:
        simultaneously jitter clean the pulse train and one of:
            count the pulses of the pulse train; and,
            monitor the puke train for a missing pulse; and,
        in response to counting a predetermined number of pulses or detecting the missing pulse, extract a jitter clean pulse from the pulse train to generate a jitter clean sync/reset pulse; and,
    an internal clock which receives the jitter clean sync/reset pulse.

2. The detector module according to claim 1, wherein the synchronization circuitry is further configured to:
    recover a clock signal from the data stream using clock recovery; and
    jitter clean the recovered clock signal.

3. The detector module according to claim 2, wherein the synchronization circuitry includes:
    a first jitter cleaner circuit which jitter cleans the recovered clock signal;
    a second jitter cleaner circuit which jitter cleans the pulse train;
    a counter circuit which counts the pulses of the pulse train; and,
    a combiner circuit which extracts the jitter clean sync reset pulse.

4. The detector module according to claim 2, wherein the synchronization circuitry includes a field-programmable gate array recovering the clock signal from the data stream.

5. The detector module according to claim 1, further including:
    a plurality of radiation sensitive elements defining a detection grid, the detection grid generating electrical pulses in response to photon strikes;
    a controller configured to:
        receive the electrical pulses from the plurality of radiation sensitive elements; and,
        in response to receiving an electrical pulse,
            generate event data identifying the location of the photon strike on the detection grid; and,
            transmit the generated event data with a time stamp determined from the internal clock to the PET processing system.

6. The detector module according to claim 5, further including:
    one or more scintillator elements generating the light photons in response to being struck by gamma photons from a region of interest (ROI) to be imaged, the scintillator elements being optically coupled to the detection grid.

7. A PET system comprising:
    a plurality of detector modules arranged around a region of interest (ROI), each according to the detector module of claim 1;
    the PET processing system optically connected to the plurality of detector modules, the PET processing system configured to:
        integrate a clock signal with the data stream, the data stream including the pulse train carrying the command to generate the sync/reset pulses; and,
        transmit the data stream simultaneously to each of the plurality of detector modules.

8. The PET system according to claim 7, wherein the PET processing system includes:
    at least one processor programmed to:
        receive event data for a plurality of events from the plurality of detector modules, event data for each event identifying the location of a photon strike on a detection grid of one of the plurality of detector modules and including a time stamp;
        identify event pairs using the time stamps of the plurality of events; and,
        reconstruct an image of the ROI from the generated event pairs, the ROI emitting the photons.

9. The PET system according to claim 7, wherein integrating the clock signal with the data stream includes encoding the data stream to increase transitions.

10. A method for synchronizing a detector module with other detector modules of a positron emission tomography (PET) system, said method comprising:
    optically receiving an optical data stream from a PET processing system, the data stream including a pulse train carrying a command to generate sync/reset pulses;
    simultaneously jitter cleaning the pulse train and one of:
        counting the pulses of the pulse train; and,
        monitoring the pulse train for a missing pulse; and,
    in response to counting a predetermined number of pulses or detecting the missing pulse, extracting a jitter clean pulse from the pulse train to generate a jitter clean sync/reset pulse; and,
    providing the jitter clean sync/reset pulse to an internal clock.

11. The method according to claim 10, further including:
    recovering a clock signal from the data stream using clock recovery; and,
    jitter cleaning the recovered clock signal.

12. The method according to claim 11, wherein jitter cleaning the recovered clock signal is performed by a first jitter cleaner circuit, jitter cleaning the pulse train is performed by a second jitter cleaner circuit, counting the pulses of the pulse train is performed a counter circuit, extracting the jitter clean sync/reset pulse is performed by a combiner circuit.

13. The method according to claim 11, wherein recovering the clock signal from the data stream is performed by a field-programmable gate array.

14. The method according to claim 10, further including:
receiving electrical pulses from a plurality of radiation sensitive elements, the plurality of radiation sensitive elements generating the electrical pulses in response to photon strikes; and,
in response to receiving an electrical pulse,
generating event data identifying the location of the photon strike on the detection grid; and,
transmitting the generated event data with a time stamp determined from the internal clock to the PET processing system.

15. A method for synchronizing a plurality of detector modules of a positron emission tomography (PET) system, said method comprising:
combining a clock signal and a pulse train carrying a command to generate a sync/reset pulse with a data stream;
optically transmitting the data stream simultaneously to each of the plurality of detector modules;
synchronizing internal clocks of the plurality of detector modules according to the method of claim 10.

16. The method according to claim 15, wherein integrating the clock signal with the data stream includes encoding the data stream to increase transitions.

17. A method for generating an image of a region of interest (ROI) using a plurality of detector modules of a positron emission tomography (PET) system, said method comprising:
synchronizing the plurality of detector modules according to claim 15;
receiving event data for a plurality of events from the plurality of detector modules, event data for each event identifying the location of a photon strike on a detection grid of one of the plurality of detector modules and including a time stamp;
generating event pairs using the time stamps of the plurality of events; and,
reconstructing an image of the ROI from the received event data, the ROI emitting the photons.

18. A positron emission tomography (PET) system comprising:
a PET processing system which generates a clock signal and sync/reset pulse information and which reconstructs a PET image from received event data, the PET processing system including optical transceivers which convert the clock signal and the sync/reset pulse information into an optical data stream and which convert optical event information into the received event data;
a plurality of detector modules disposed to received gamma photons form an examination region, each detector module including:
a transceiver which converts light signals to electrical signals;
synchronization circuitry which extracts the clock signal and the sync/reset pulses from the electrical signals; wherein the synchronization circuitry is configured to:
simultaneously jitter clean a pulse train of the electrical signals and count the pulses of the pulse train; and,
in response to counting a predetermined number of pulses, extract a jitter clean pulse from the pulse train to generate a jitter clean sync/reset pulse provided to the clock;
a clock which is sync/reset with the clock signal and the sync/reset pulses;
a detector grid which converts the received gamma photons into event data;
the transceiver further converts the event data and information of locations at which the gamma photon were received and a time stamp from the clock into the optical event information;
a plurality of optical fibers connecting the PET processing system with each of the detector modules to carry the optical data stream simultaneously to the detector modules and the optical event information from each detector module to the PET processing system.

19. The PET system according to claim 18, wherein the synchronization circuitry is configured to:
simultaneously jitter clean a pulse train of the electrical signals and monitor the pulse train for a missing pulse; and,
in response to detecting the missing pulse, extract a jitter clean pulse from the pulse train to generate a jitter clean sync/reset pulse provided to the clock.

* * * * *